United States Patent
Visscher et al.

[19]

[11] Patent Number: 5,919,181
[45] Date of Patent: *Jul. 6, 1999

[54] PRE-FOLDED ABSORBENT ARTICLES HAVING IMPROVED FIT

[75] Inventors: Ronald Bosman Visscher; Kenneth Barclay Buell; Thomas Ward Osborn, III, all of Cincinnati, Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/854,786

[22] Filed: May 12, 1997

Related U.S. Application Data

[63] Continuation of application No. 08/602,694, Feb. 16, 1996, abandoned, which is a continuation of application No. 08/276,239, Jul. 18, 1994, abandoned.

[51] Int. Cl.$^6$ ..................................................... A61F 13/15
[52] U.S. Cl. ....................... 604/387; 604/385.1; 604/378
[58] Field of Search ..................... 604/366, 372, 604/378, 379, 377, 380, 381, 387, 385.1, 389

[56] References Cited

U.S. PATENT DOCUMENTS

| | | |
|---|---|---|
| 3,605,746 | 9/1971 | Scharr . |
| 3,848,595 | 11/1974 | Endres . |
| 4,067,336 | 1/1978 | Johnson .................................. 128/284 |
| 4,182,334 | 1/1980 | Johnson .................................. 128/287 |
| 4,195,634 | 4/1980 | DiSalvo . |
| 4,327,732 | 5/1982 | Thinner . |
| 4,595,392 | 6/1986 | Johnson et al. . |
| 4,648,861 | 3/1987 | Pierce . |
| 4,655,759 | 4/1987 | Romans-Hess et al. . |
| 4,687,478 | 8/1987 | Van Tilburg . |
| 4,701,177 | 10/1987 | Ellis et al. . |
| 4,804,380 | 2/1989 | Lassen et al. . |
| 4,946,454 | 8/1990 | Schmidt . |
| 5,032,121 | 7/1991 | Mokry . |
| 5,057,096 | 10/1991 | Faglione . |
| 5,171,302 | 12/1992 | Buell .................................... 604/385.1 |

FOREIGN PATENT DOCUMENTS

| | | |
|---|---|---|
| 0 136524 | 10/1985 | European Pat. Off. . |
| 0 687 453 A1 | 12/1995 | European Pat. Off. . |
| 0 850628 | 7/1998 | European Pat. Off. . |

*Primary Examiner*—John G. Weiss
*Assistant Examiner*—Dennis Ruhl
*Attorney, Agent, or Firm*—Theodore P. Cummings; Jeffrey V. Bamber; Jacobus C. Rasser

[57] ABSTRACT

The present invention relates to absorbent articles comprising a plurality of bend lines which are predisposed on either or both ends of the article to bend upon encountering the lateral compressive forces caused by the thighs of the wearer, the bend lines comprising, a main rear bend line centrally and longitudinally disposed on the article beginning at a point about one-eighth to about one-half of the distance away from the front edge and extending toward the back edge of the article;

a main front bend line or lines centrally and longitudinally disposed on the article beginning about the front edge and extending up to the beginning point of the main rear fold line, or comprising two parallel fold lines longitudinally disposed on the article beginning at about the front edge and extending to about the beginning of the main rear bend line, or comprising two parallel bend lines longitudinally disposed on the article beginning at about the front edge and extending for about one-fourth to about two-thirds of the full length of the article from the front edge; and two rearwardly diverging bend lines starting at about the beginning point of the main rear fold line, the rearwardly diverging fold lines extending toward each side of the longitudinal edges of the article, the rearwardly diverging bend lines each forming an angle with the longitudinal centerline of from about 10° to about 80°;

wherein the body facing surface is "V" or "U" shaped in the front region and is inverted "V" or "U" shaped in the rear region of the article.

47 Claims, 5 Drawing Sheets

PRE-FOLDED ABSORBENT ARTICLES HAVING IMPROVED FIT

This is a continuation of application Ser. No. 08/602,694, filed on Feb. 16, 1996, now abandoned, which is a continuation of application Ser. No. 08/276,239, filed on Jul. 18, 1994, now abandoned.

TECHNICAL FIELD

The present invention relates to absorbent articles having a plurality of bend lines, specifically female sanitary napkins. Particularly the present invention relates to sanitary napkins offering enhanced fit and potentially reduced leakage through a distinct pattern of embossed channels, folds, or creases which are activated through compression by the thighs of the wearer to generate a specific pad configuration.

BACKGROUND OF THE INVENTION

With respect to sanitary napkins, at least three general classes of design exits. One such design includes those sanitary napkins which are generally cupped or boat-shaped and which are intended to catch menses as it runs or drips from the vaginal orifice. Sanitary napkins of this class are disclosed in U.S. Pat. No. 4,655,759, entitled "Reduced Leakage Menstrual Pad With Built-in Fold Lines", Romans-Hess et al., issued on Apr. 7, 1987.

A second class of design includes those that are raised upwardly or humped in their medial portions so to be near or in contact with the pudendal region when worn. Sanitary napkins of this class are disclosed in U.S. Pat. No. 4,701,177, entitled "Three-Dimensional Shaped Feminine Pad With Narrow, Absorbent Center and Winged Edges", Ellis et al., issued on Oct. 20, 1987.

The third class of sanitary napkin design includes those that are not predisposed to have a trough or a hump shape when worn, but instead have a more or less rope-like shape when worn. Such sanitary napkins typically have a fluff pulp absorbent core surrounded by flexible outer wraps. When the sanitary napkin is subjected to compressive forces from the wearer's thighs, the fluff pulp core simply compacts or bunches into an arbitrary, but generally rope-like shape. Sanitary napkins of this class are disclosed in U.S. Pat. No. 4,687,478, entitled "Shaped Sanitary Napkin With Flaps", Van Tilburg, issued on Aug. 18, 1987. Attempts have been made to prevent the bunching effect of such compaction type sanitary napkins by providing them with a form-retaining member. Such sanitary napkins are disclosed in U.S. Pat. No. 4,195,634, entitled "Sanitary Napkin with Resilient Stiffening Means", DiSalvo et al., issued on Apr. 1, 1980.

All of the above references are herein incorporated by reference in their entirety.

While the sanitary napkins and other devices discussed above do provide some measure of success in absorbing and containing body exudates, they fail to provide a sanitary napkin which closely conforms to and fits the cross-sectional outline of the pudendal region as soon as applied without requiring the usual bending, twisting or other adjustments or manipulations. Also, they fail to provide a sanitary napkin which will always retain such conformity simply due to its reformable and resilient characteristics.

Therefore, the object of the present invention is to provide an absorbent article which closely conforms to and fits the cross-sectional outline of the external surfaces of the pudendal region.

Therefore, the object of the present invention is to provide an absorbent article, preferably an ultra thin napkin for panties, with a plurality of bend lines (i.e., embossed channels, folds and/or creases), with a body facing surface wherein the body facing surface has both a convex upward configuration and a convex downward configuration when the napkin is subjected to the lateral compressive forces of the wearer's thighs. Preferably the absorbent article has a plurality of predisposed bend regions.

Another object of the present invention is to provide an absorbent article, preferably an ultra thin napkin, with a plurality of bend lines (i.e., embossed channels, folds and/or creases), with a body facing surface, wherein the body facing surface is "V" or "U" shaped in the front region and inverted "V" or "U" shaped in the rear region when the napkin is subjected to the lateral compressive forces of the wearer's thighs. Preferably the absorbent article has a plurality of pre-established bend lines, has a uniform thickness of from about 1 mm to about 13 mm, preferably from about 2 mm to about 8 mm and is substantially rectangular, with rounded corners.

SUMMARY OF THE INVENTION

The present invention relates to a sanitary absorbent article, i.e., a sanitary napkin and/or a liner for panties, which is structurally predisposed to form a transverse flexure line which relieves and controls the stress of upward rear folding and downward frontal cupping.

Specifically the present invention relates to absorbent articles comprising:

A. a liquid pervious topsheet;
B. a liquid impervious backsheet joined with the topsheet;
C. an absorbent element between the topsheet and the backsheet;

wherein the article has a body surface, a garment surface, a front edge, a back edge, two longitudinal edges, a longitudinal centerline within the plane of the sanitary napkin which is aligned with a vertical plane which bisects a standing wearer into left and right halves when the article is worn, and wherein the article has a plurality of bend lines which are predisposed to form a different configuration with the lateral compressive forces caused by the thighs of the wearer, the bend lines comprising:

a main rear bend line centrally and longitudinally disposed on the article beginning at a point about one-eighth to about one-half, preferably about 2" or one-forth to about one-half, more preferably about one-third to about one-half, of the distance away from the front edge and extending toward the back edge of the article, preferably extending at least about two-thirds of the way or more from the front edge to the back edge of the article;

a main front bend line or lines centrally and longitudinally disposed on the article beginning at about the front edge and extending up to about the beginning point of the main rear bend line, or comprising two parallel fold lines longitudinally disposed on the article beginning at about the front edge and extending to about the beginning of the main rear bend line, or comprising two parallel bend lines longitudinally disposed on the article beginning at about the front edge and extending for about one-forth to about two-thirds of the full length of the article from the front edge; and two rearwardly diverging bend lines starting at about the beginning point of the main rear fold line, the rearwardly diverging bend lines extending toward each side of the longitudinal edges of the article, the rearwardly diverging bend lines each forming an angle with the longitudinal centerline of from about 10° to about 80°, preferably from about 15° to about 60°, more preferably from about 20° to about 45°; and wherein the main rear bend line is folded outwardly so that the portions of the garment surface on opposite sides of the main rear bend line are brought closer together; and the main front bend line or lines and the two rearwardly diverging bend lines are folded inwardly so that the portions of the body surface on opposite sides of the main front bend line and the two rearwardly diverging bend lines are brought closer together. Preferably, the article has an indicia located on the body surface side of the article (described hereinafter) toward the front edge.

DETAILED DESCRIPTION

Figure 1:
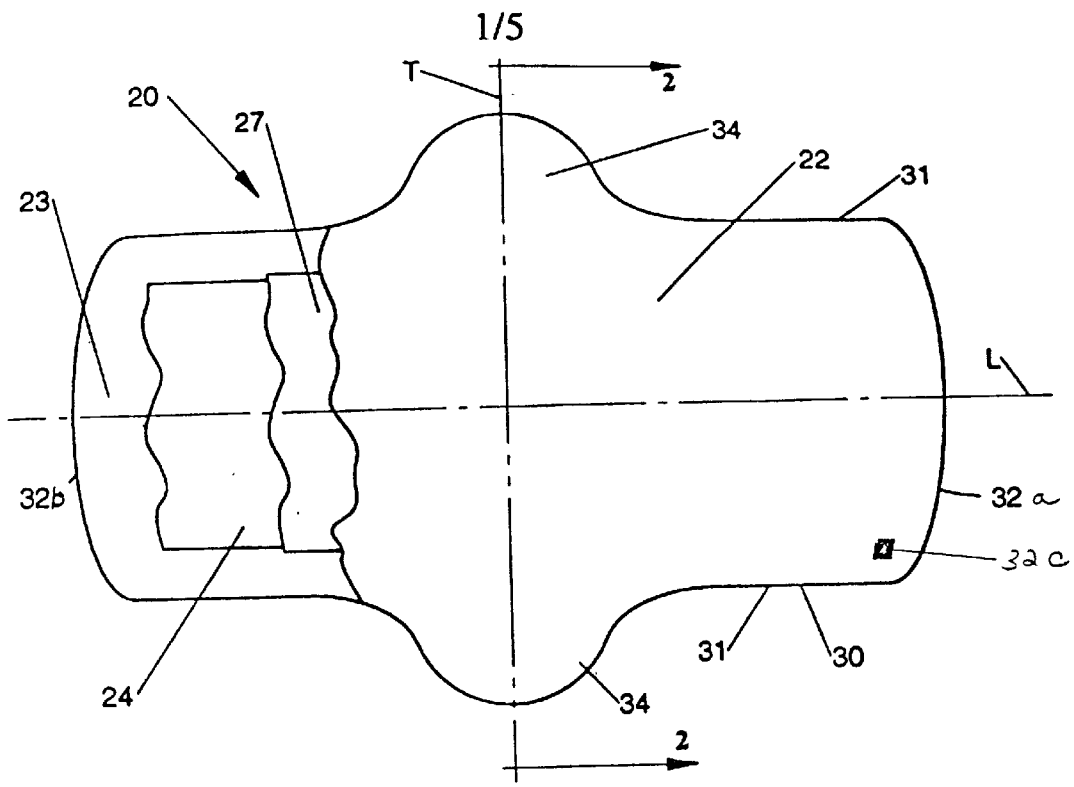
FIG. 1 is a plain view of the sanitary napkin 20 of the present invention in its flat out state with the body-contacting surface, 20a, oriented towards the viewer.

Articles of the present invention can be made by constituents which are well known in the art. Also, methods and apparatus for assembling catamenials are also known in the art. Not intending to be limiting, the following exemplifies the articles of the present invention.

The present invention relates to a sanitary absorbent article, i.e., a sanitary napkin and/or a liner for panties, which is structurally predisposed to form a transverse flexure line which relieves and controls the stress of upward rear folding and downward frontal cupping.

Specifically the present invention relates to absorbent articles comprising:

A. a liquid pervious topsheet;

B. a liquid impervious backsheet joined with the topsheet;

C. an absorbent element between the topsheet and the backsheet;

wherein the article has a body surface, a garment surface, a front edge, a back edge, two longitudinal edges, a longitudinal centerline within the plane of the sanitary napkin which is aligned with a vertical plane which bisects a standing wearer into left and right halves when the article is worn, and wherein the article has a plurality of bend lines which are predisposed to form a different configuration with the lateral compressive forces caused by the thighs of the wearer, the bend lines comprising:

a main rear bend line centrally and longitudinally disposed on the article beginning at a point about one-eighth to about one-half, preferably about 2" or one-forth to about one-half, more preferably about one-third to about one-half, of the distance away from the front edge and extending toward the back edge of the article, preferably extending at least about two-thirds of the way or more from the front edge to the back edge of the article;

a main front bend line or lines centrally and longitudinally disposed on the article beginning at about the front edge and extending up to about the beginning point of the main rear bend line, or comprising two parallel fold lines longitudinally disposed on the article beginning at about the front edge and extending to about the beginning of the main rear bend line, or comprising two parallel bend lines longitudinally disposed on the article beginning at about the front edge and extending for about one-forth to about two-thirds of the full length of the article from the front edge; and two rearwardly diverging bend lines starting at about the beginning point of the main rear fold line, the rearwardly diverging bend lines extending toward each side of the longitudinal edges of the article, the rearwardly diverging bend lines each forming an angle with the longitudinal centerline of from about 10° to about 80°, preferably from about 15° to about 60°, more preferably from about 20° to about 45°; and wherein the main rear bend line is folded outwardly so that the portions of the garment surface on opposite sides of the main rear bend line are brought closer together; and the main front bend line or lines and the two rearwardly diverging bend lines are folded inwardly so that the portions of the body surface on opposite sides of the main front bend line and the two rearwardly diverging bend lines are brought closer together. Preferably, the article has an indicia located on the body surface side of the article (described hereinafter) toward the front edge.

As used herein, the term "absorbent article" refers to devices which absorb and contain body exudates, and, more specifically, refers to devices which are placed against or in proximity to the body of the wearer to absorb and contain the various exudates discharged from the body. A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

FIG. 1 is a plain view of the sanitary napkin 20 of the present invention in its planar state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 22, a liquid impervious backsheet 23 joined with the topsheet 22, an absorbent core 24 positioned between the topsheet 22 and the backsheet 23.

Figure 3:
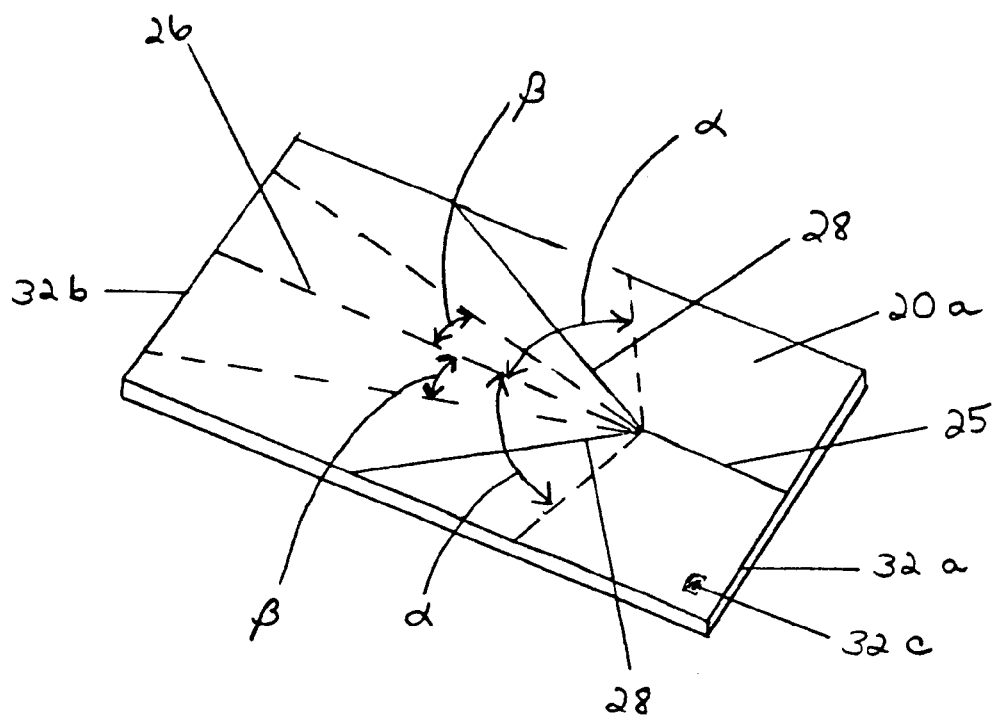
FIG. 3 is a plain view of the sanitary napkin with the bend lines illustrated.
Figure 4:
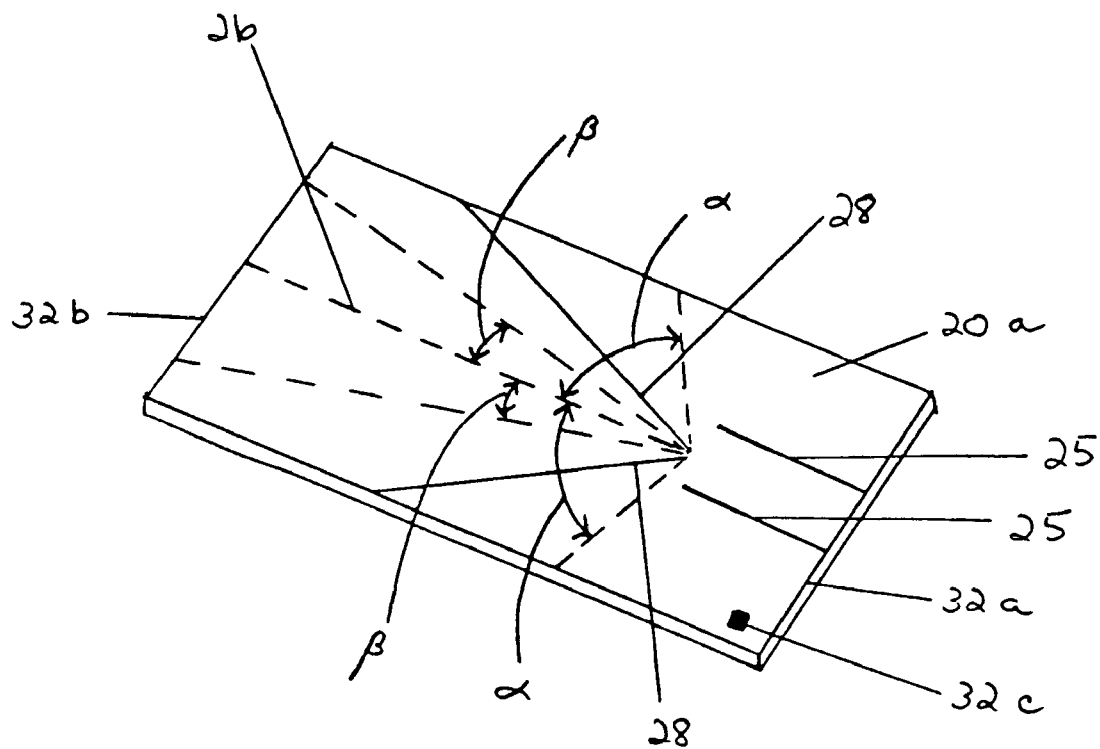
FIG. 4 is a plain view of the sanitary napkin with the bend lines illustrated.

The sanitary napkin 20 has two surfaces, a body-contacting surface or "body surface" 20a and a garment surface 20b. The sanitary napkin 20 is shown in FIG. 1, FIG. 3, and FIG. 4, as viewed from its body contacting surface 20a. The body contacting surface 20a is intended to be worn adjacent to the body of the wearer while the garment surface 20*b* is on the opposite side and is intended to be placed adjacent to the wearer's undergarments when the sanitary napkin 20 is worn. The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies in the plane of the sanitary napkin 20 that is generally perpendicular to the longitudinal direction.

FIG. 1 also shows that the sanitary napkin 20 has a periphery 30, which is defined by the outer edges of the sanitary napkin 20 in which the longitudinal edges are designated 31 and the end edges are designated 32, the front edge being 32*a* and the back edge being 32*b*. An indicia 32*c* is located on the body surface 20*a* in the area anywhere from the front edge to one-fourth of the length of the article away from the front edge. The indicia 32*c* is any type of marking or designation (i.e. any small shape or design allows the wearer to know which end edge is the front edge so that they can properly position the article initially and properly wear the article.

While the topsheet, the backsheet, and the absorbent core may be assembled in a variety of well known configurations (including so called "tube" products or side flap products), preferred sanitary napkin configurations are described generally in U.S. Pat. No. 4,950,264, "Thin, Flexible Sanitary Napkin," Osborn, issued on Aug. 21, 1990; U.S. Pat. No. 4,425,130, "Compound Sanitary Napkin," DesMarais, issued on Jan. 10, 1984; U.S. Pat. No. 4,321,924, "Bordered Disposable Absorbent Article," Ahr, issued on Mar. 30, 1982; U.S. Pat. No. 4,589,876, "Shaped Sanitary Napkin With Flaps", Van Tilburg, issued on Aug. 18, 1987. Each of these patents are incorporated herein by reference.

FIG. 1 shows a preferred embodiment of the sanitary napkin 20 in which the topsheet 22 and the backsheet 23 have length and width dimensions generally larger than those of the absorbent core 24. The topsheet 22 and the backsheet 23 extend beyond the edges of the absorbent core 24 to thereby form not only portions of the periphery but also side flaps or wings 34.

Figure 2:
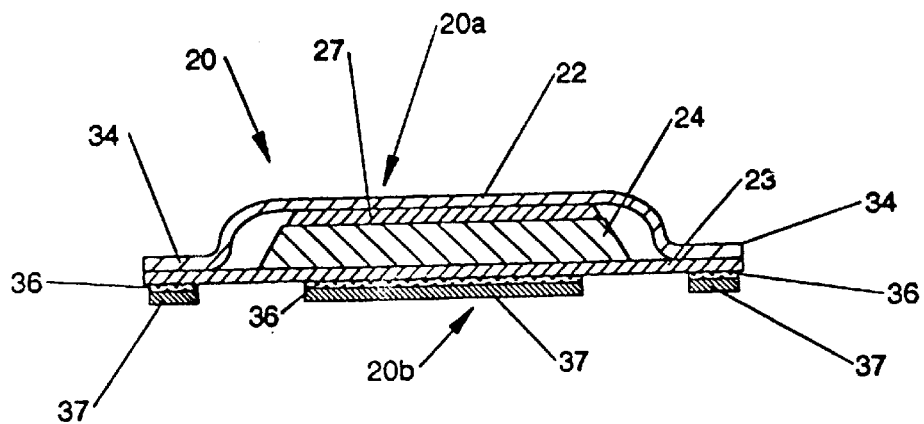
FIG. 2 is a cross-sectional view of the sanitary napkin 20 taken along line 2—2 of FIG. 1.

FIG. 2 is a cross-sectional view of the sanitary napkin 20 taken along section line 2—2 of FIG. 1. FIG. 2 shows the secondary topsheet 27, just below the topsheet 22. The wing 34 is an extension of the topsheet 22. The fastening means 36 together with the release liner 37 maintains the article in place so that it can perform its intended function.

FIG. 3 and FIG. 4 are also plain views of the sanitary napkin 20 of the present invention with the portion of the sanitary napkin 20 which faces or contacts the wearer, oriented toward the viewer. The main front bend line 25 begins at the front edge 32*a* and extends to about the beginning point of the main rear bend line 26. The two rearwardly diverging bend lines 28 also begin at about the beginning point of the main rear fold line 26, extending towards the back edge 32*b*. The rearwardly diverging bend lines 28 each form an angle with the longitudinal centerline L of from about 10°, the angle represented by $\beta$, to about 80°, the angle represented by $\alpha$, in FIGS. 3 and 4.

FIG. 4 represents a sanitary napkin 20 where the main front bend line 25 comprises two parallel fold lines longitudinally disposed on the article.

Figure 5:
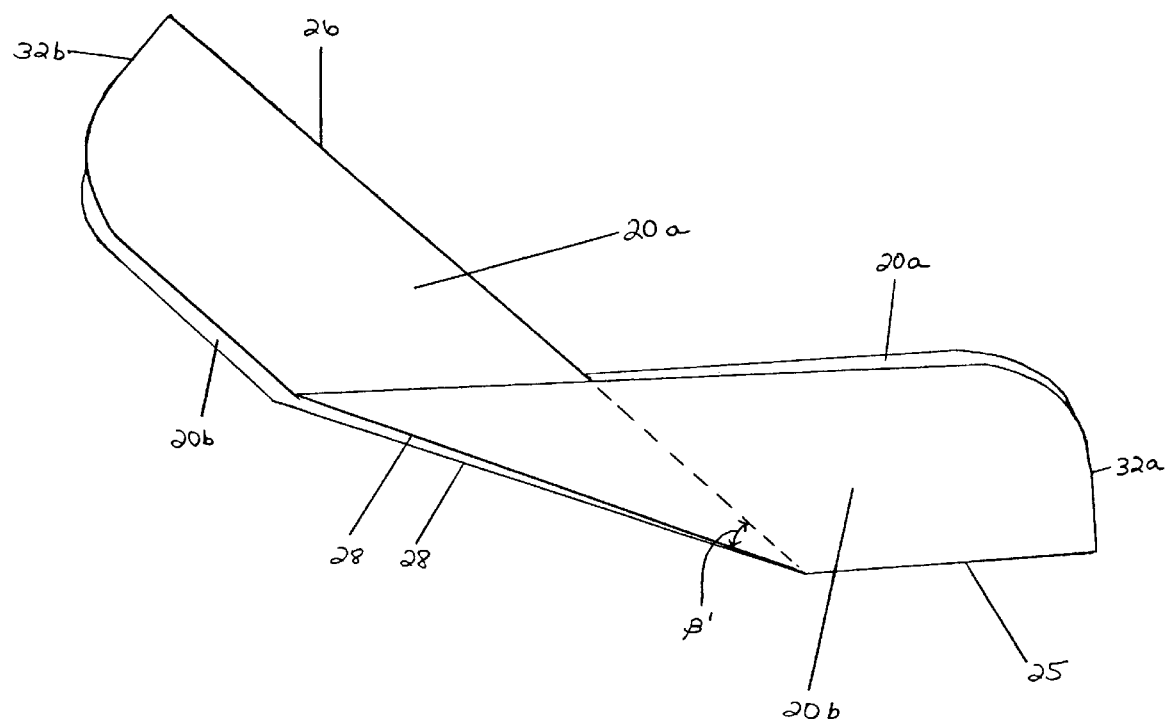
FIG. 5 is a perspective view of the pad under lateral compression to show the configuration formed by the pad.
Figure 6:
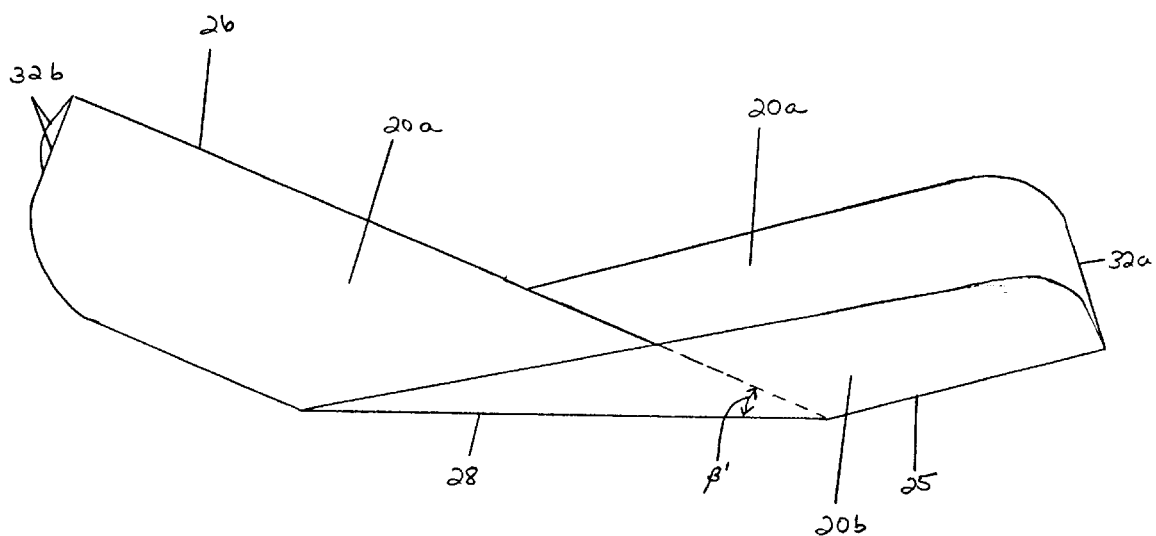
FIG. 6 is a perspective view of the pad under lateral compression to show the configuration formed by the pad.

FIG. 5 and FIG. 6 are side views of a preferred folded sanitary napkin 20, which is 8 inches long with rounded corners wherein $\beta$ is approximately 20°.

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 is manufactured from a wide range of materials such as woven and nonwoven materials, polymeric materials such as apertured formed thermoplastic films, apertured plastic films, apertured hydroformed thermoplastic films; reticulated thermoplastic films; and thermoplastic scrims, porous films, reticulated foams, etc. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The preferred topsheets of the present invention are described in detail in U.S. Pat. No. 4,342,314 entitled "Resilient Plastic Web Exhibiting Fiber-Like Properties," Radel et al., issued on Aug. 3, 1982, which is herein incorporated by reference in its entirety, especially column 4, line 41 to column 6, line 44. The preferred method of making the topsheets of the present invention is disclosed in U.S. Pat. No. 4,637,819, Ouellette et al., issued on Jan. 20, 1987, which is herein incorporated by reference.

The preferred apertured topsheets of the present invention are pervious to body exudates and yet are non-absorbent and have a reduced tendency to allow liquids to pass back through and rewet the wearer's skin. Thus, the surface of the apertured topsheet which is in contact with the body remains dry, thereby reducing body soiling and creating a more comfortable feel for the wearer.

Other formed films are described in U.S. Pat. No. 3,929,135, entitled "Absorptive Structures Having Tapered Capillaries," Thompson, issued on Dec. 30, 1975; U.S. Pat. No. 4,324,246 entitled "Disposable Absorbent Article Having A Stain Resistant Topsheet", Mullane, et al., issued on Apr. 13, 1982; U.S. Pat. No. 4,463,045 entitled "Macroscopically Expanded Three-Dimensional Plastic Web Exhibiting Non-Glossy Visible Surface and ClothLike Tactile Impression", Ahr et al., issued on Jul. 31, 1984; and U.S. Pat. No. 5,006,394 "Multilayer Polymeric Film", Baird, issued on Apr. 9, 1991. Each of these patents are incorporated herein by reference in their entirety. Other preferred topsheets for the present invention are the formed film described in one or more of the above patents and marketed on sanitary napkins by The Procter & Gamble Company of Cincinnati, Ohio as "DRI-WEAVE".

In a preferred embodiment of the present invention, the body surface of the topsheet is hydrophilic so as to help liquid to transfer through the topsheet faster than if the body surface was not hydrophilic. This will diminish the likelihood that menstrual fluid and perspiration will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet," Aziz, et al., filed on Nov. 19, 1991, which is incorporated herein by reference in its entirety.

Alternatively, the body surface of the topsheet can be made hydrophilic by treating it with a surfactant such as is described in the above referenced U.S. Pat. No. 4,950,254, incorporated herein by reference.

The absorbent core 24 may be any absorbent means which is capable of absorbing or retaining liquids (e.g., menses and/or urine). The absorbent core 24 may be manufactured in a wide variety of sizes and shapes (e.g., rectangular, oval, hourglass, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including conform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones) (e.g., profiled so as to be thicker in the center), hydrophilic gradients, superabsorbent gradients, or lower density and lower average basis weight acquisition zones; or may comprise one or more layers or structures. The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins. Preferably the absorbent articles of the present invention are sanitary napkins which are uniform in thickness.

Exemplary absorbent structures for use as the absorbent core of the present invention are described in U.S. Pat. No. 4,950,264 entitled "Thin, Flexible Sanitary Napkin", Osborn, issued on Aug. 21, 1990; U.S. Pat. No. 4,610,678, entitled "High-Density Absorbent Structures", Weisman et al., issued Sep. 9, 1986; U.S. Pat. No. 4,834,735, entitled "High Density Absorbent Members Having Lower Density and Lower Basis Weight Acquisition Zones", Alemany et al., issued on May 30, 1989; European Patent Application No. 198,683, P&G, Duenk, et al., published on Oct. 22, 1986, all of which are incorporated herein by reference in their entirety.

The backsheet 23 and the topsheet 22 are positioned adjacent the garment surface 20b and the body surface 20a, respectively, of the absorbent core 24 and are preferably joined thereto and to each other by attachment means (not shown) such as those well known in the art. For example, the backsheet 23 and/or the topsheet 22 may be secured to the absorbent core 24 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference in their entirety. Alternatively, the attachment means may comprise heat bonds, pressure bonds, ultrasonic bonds, dynamic mechanical bonds, or any other suitable attachment means or combinations of these attachment means as are known in the art.

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means, fastening means, or attachment means well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697 incorporated herein by reference. Before the sanitary napkin is placed in use, the pressure-sensitive adhesive is typically covered with a removable release liner 37 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The sanitary napkin 20 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps 34 each of which are adjacent to and extend laterally from the side edge of the absorbent core. The flaps are configured to drape over the edges of the wearer's panties in the crotch region so that the flaps are disposed between the edges of the wearer's panties and the thighs. The flaps serve three purposes. First, the flaps help to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty.

The flaps can be constructed of various materials including materials similar to the topsheet, backsheet, core, or combination of these materials, but preferably is constructed of the topsheet materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986, all of which are incorporated herein by reference in their entirety.

In a preferred embodiment of the present invention, an acquisition layer(s) 27 may be positioned between the topsheet and the absorbent core. The acquisition layer 27 may serve several functions including improving wicking of exudates over and into the absorbent core. There are several reasons why the improved wicking of exudates is important, including providing a more even distribution of the exudates throughout the absorbent core and allowing the sanitary napkin 20 to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S, Pat. No. 4,950,264 issued to Osborn. All of the above references are incorporated herein by reference.

In a preferred embodiment, the acquisition layer may be joined with the topsheet by any of the conventional means for joining webs together, most preferably by fusion bonds.

While particular embodiments of the present invention have been illustrated and described, various other changes and modifications can be made without departing from the spirit and scope of the invention. Therefore the claims cover all such changes and modifications that are within the scope of this invention.

What is claimed is:

1. A pre-folded absorbent article having a pre-folded configuration within said absorbent article producing a convex portion positioned adjacent to a wearer's pudendal groove and a concave portion folded away from a wearer's perineum consisting of:

A. a liquid pervious topsheet;
   B. a liquid impervious backsheet joined with the topsheet;
   C. an absorbent element positioned between the topsheet and the backsheet;
   wherein the article has a body surface, a garment surface, a front edge, a back edge, two longitudinal edges, a longitudinal centerline within the plane of the absorbent article aligned with a vertical plane bisecting a standing wearer into left and right halves when the article is worn, and wherein the article has a plurality of bend lines which are predisposed on at least one end of the article to bend upon encountering the lateral compressive forces caused by a wearer's thighs, the plurality of bend lines comprising, on at least one end of the article:
   a main rear bend line centrally and longitudinally disposed on the article at a beginning point proximately disposed about one-eighth to about one-half of the distance away from the front edge and extending toward the back edge of the article, said main rear bend line forming said convex portion of said article and being positioned to fit within said wearer's pudendal groove;
   a main front bend line centrally and longitudinally disposed on the article beginning at about the front edge and extending up to the beginning point of the main rear bend line, said main front bend line forming said concave portion of said article and being positioned to fit away from said perineum of said wearer; and
   two rearwardly diverging bend lines starting at about the beginning point of the main rear bend line, the rearwardly diverging bend lines extending toward each side of the longitudinal edges of the article, the rearwardly diverging bend lines each forming an angle with the longitudinal centerline of from about 10° to about 80°;
   wherein the main rear bend line folds so that the portions of the garment surface on opposite sides of the main rear bend line are brought closer together to provide a raised portion along the main rear bend line adapted to be in intimate contact with a user's body; and the main front bend line and the two rearwardly diverging bend lines fold so that the portions of the body surface on opposite sides of the main front bend line and the two rearwardly diverging bend lines are brought closer together to provide a recessed portion along the main front bend line adapted to be remote from a user's body, and wherein said topsheet, said backsheet, and said absorbent core provide said pre-folded configuration to said absorbent article.

2. The article of claim 1 wherein the bend lines are selected from the group consisting of pre-established fold lines, embossed channels or mixtures thereof.

3. The article of claim 2 wherein the bend lines form a "V" shape with the main front bend line and an inverted "V" shape with the main rear bend line.

4. The article of claim 2 wherein the thickness of the article is from about 1 mm to about 13 mm.

5. The article of claim 4 wherein the thickness of the article is uniform throughout its length.

6. The article of claim 2 wherein the main rear bend line begins at a point about one-fourth to about one-half of the distance away from the front edge and extends to about the rear edge of the article; the main front bend line begins at about the front edge and extends up to about the beginning point of the main rear bend line; and wherein the two rearwardly diverging bend lines start at about the beginning point of the main rear bend line, the rearwardly diverging bend lines each forming an angle with the longitudinal centerline of from about 15° to about 60°.

7. The article of claim 6 wherein the rearwardly diverging bend lines each form an angle with the longitudinal centerline of from about 20° to about 45°.

8. The article of claim 2 wherein the main rear bend line begins at a point about one-fourth to about one-half of the distance away from the front edge and extends to about the rear edge of the article; the main front bend line comprises two parallel bend lines beginning at about the front edge and extending to about the beginning of the main rear bend line, and wherein the two rearwardly diverging bend lines start at about the beginning point of the main rear bend line, the rearwardly diverging bend lines each forming an angle with the longitudinal centerline of from about 15° to about 60°.

9. The article of claim 6 wherein the rearwardly diverging bend lines each form an angle with the longitudinal centerline of from about 20° to about 45°.

10. The article of claim 2 wherein the main rear bend line begins at a point about one-third to about one-half of the distance away from the front edge and extends to about the rear edge of the article; the main front bend line begins at about the front edge and extends up to about the beginning point of the main rear bend line; and wherein the two rearwardly diverging bend lines start at about the beginning point of the main rear bend line, the rearwardly diverging bend lines each forming an angle with the longitudinal centerline of from about 15° to about 60°.

11. The article of claim 10 wherein the rearwardly diverging bend lines each form an angle with the longitudinal centerline of from about 20° to about 45°.

12. The article of claim 2 wherein the main rear bend line begins at a point about one-third to about one-half of the distance away from the front edge and extends to about the rear edge of the article; the main front bend line comprises two parallel bend lines beginning at about the front edge and extending to about the beginning of the main rear bend line, and wherein the two rearwardly diverging bend lines start at about the beginning point of the main rear bend line, the rearwardly diverging bend lines each forming an angle with the longitudinal centerline of from about 15° to about 60°.

13. The article of claim 12 wherein the rearwardly diverging bend lines each form an angle with the longitudinal centerline of from about 20° to about 45°.

14. The article of claim 2 wherein the bend lines form a "U" shape with the main front bend line and an inverted "U" shape with the main rear bend line.

15. The article of claim 2 wherein the bend lines form a "U" shape and a "V" shape with the main front and main rear bend lines.

16. A pre-folded absorbent article having a pre-folded configuration producing a convex portion positioned adjacent to a wearer's pudendal groove and a concave portion folded away from a wearer's perineum, said absorbent article consisting of a body surface, a garment surface, a first edge, a back edge, two longitudinal edges, a longitudinal centerline, a liquid pervious topsheet, a liquid impervious backsheet joined to the topsheet, and an absorbent element positioned between the topsheet and the backsheet, said absorbent article being provided with a plurality of predisposed bend lines along which the absorbent article folds upon encountering the lateral compressive forces caused by a wearer's thighs, the plurality of bend lines consisting of:

a main rear bend line centrally and longitudinally disposed on the absorbent article at a beginning point proximately disposed about one-eighth to about one-half of the distance away from the front edge and extending toward the back edge of the article, said main rear bend line forming said convex portion of said article and being positioned to fit within said wearer's pudendal groove;

a main front bend line centrally and longitudinally disposed in the absorbent article beginning about the front edge and extending up to the beginning point of the main rear bend line, said main front bend line forming said concave portion of said article and being positioned to fit away from said perineum of said wearer; and two rearwardly diverging bend lines starting at about the beginning point of the main rear bend line, the rearwardly diverging bend lines extending toward each side of the longitudinal edges of the article, the rearwardly diverging bend lines each forming an angle with the longitudinal centerline of from about 10° to about 80°;

wherein the main rear bend line folds so that the portions of the garment surface on opposite sides of the main rear bend line are brought closer together to provide a raised portion along the main rear bend line adapted to be in intimate contact with a user's body; and the main front bend line and the two rearwardly diverging bend lines fold so that the portions of the body surface on opposite sides of the main front bend line and the two rearwardly diverging bend lines are brought closer together to provide a recessed portion along the main front bend line adapted to be remote from a user's body, and wherein said topsheet, said backsheet, and said absorbent core provide said pre-folded configuration to said absorbent article.

17. The article of claim 16 wherein the bend lines are selected from the group consisting of pre-established fold lines, embossed channels or mixtures thereof.

18. The article of claim 17 wherein the bend lines form a "V" shape with the main front bend line and an inverted "V" shape with the main rear bend line.

19. The article of claim 17 wherein the thickness of the article is from about 1 mm to about 13 mm.

20. The article of claim 19 wherein the thickness of the article is uniform throughout its length.

21. The article of claim 17 wherein the main rear bend line begins at a point about one-fourth to about one-half of the distance away from the front edge and extends to about the rear edge of the article; the main front bend line begins at about the front edge and extends up to about the beginning point of the main rear bend line; and wherein the two rearwardly diverging bend lines start at about the beginning point of the main rear bend line, the rearwardly diverging bend lines each forming an angle with the longitudinal centerline of from about 15° to about 60°.

22. The article of claim 21 wherein the rearwardly diverging bend lines each form an angle with the longitudinal centerline of from about 20° to about 45°.

23. 7 The article of claim 17 wherein the main rear bend line begins at a point about one-fourth to about one-half of the distance away from the front edge and extends to about the rear edge of the article; the main front bend line comprises two parallel bend lines beginning at about the front edge and extending to about the beginning of the main rear bend line, and wherein the two rearwardly diverging bend lines start at about the beginning point of the main rear bend line, the rearwardly diverging bend lines each forming an angle with the longitudinal centerline of from about 15° to about 60°.

24. The article of claim 21 wherein the rearwardly diverging bend lines each form an angle with the longitudinal centerline of from about 20° to about 45°.

25. The article of claim 17 wherein the main rear bend line begins at a point about one-third to about one-half of the distance away from the front edge and extends to about the rear edge of the article; the main front bend line begins at about the front edge and extends up to about the beginning point of the main rear bend line; and wherein the two rearwardly diverging bend lines start at about the beginning point of the main rear bend line, the rearwardly diverging bend lines each forming an angle with the longitudinal centerline of from about 15° to about 60°.

26. The article of claim 25 wherein the rearwardly diverging bend lines each form an angle with the longitudinal centerline of from about 20° to about 45°.

27. The article of claim 25 wherein the main rear bend line begins at a point about one-third to about one-half of the distance away from the front edge and extends to about the rear edge of the article; the main front bend line comprises two parallel bend lines beginning at about the front edge and extending to about the beginning of the main rear bend line, and wherein the two rearwardly diverging bend lines start at about the beginning point of the main rear bend line, the rearwardly diverging bend lines each forming an angle with the longitudinal centerline of from about 15° to about 60°.

28. The article of claim 27 wherein the rearwardly diverging bend lines each form an angle with the longitudinal centerline of from about 20° to about 45°.

29. The article of claim 17 wherein the bend lines form a "U" shape with the main front bend line and an inverted "U" shape with the main rear bend line.

30. The article of claim 17 wherein the bend lines form a "U" shape and a "V" shape with the main front and main rear bend lines.

31. A pre-folded absorbent article having side edges, longitudinal edges and a pre-folded configuration within said absorbent article producing a convex portion positioned adjacent to a wearer's pudendal groove and a concave portion folded away from a wearer's perineum consisting of:

A. a liquid pervious topsheet;

B. a liquid impervious backsheet joined with the topsheet;

C. an absorbent element positioned between the topsheet and the backsheet;

D. a pair of flaps extending from the side edges of the pre-folded absorbent article;

wherein the article has a body surface, a garment surface, a front edge, a back edge, two longitudinal edges, a longitudinal centerline within the plane of the absorbent article aligned with a vertical plane bisecting a standing wearer into left and right halves when the article is worn, and wherein the article has a plurality of bend lines which are predisposed on at least one end of the article to bend upon encountering the lateral compressive forces caused by a wearer's thighs, the plurality bend lines comprising, on at least one end of the article:

a main rear bend line centrally and longitudinally disposed on the article at a beginning point proximately disposed about one-eighth to about one-half of the distance away from the front edge and extending toward the back edge of the article, said main rear bend line forming said convex portion of said article and being positioned to fit within said wearer's pudendal groove;

a main front bend line centrally and longitudinally disposed on the article beginning at about the front edge and extending up to the beginning point of the main rear bend line, said main front bend line forming said concave portion of said article and being positioned to fit away from said perineum of said wearer; and two rearwardly diverging bend lines starting at about the beginning point of the main rear bend line, the rearwardly diverging bend lines extending toward each side of the longitudinal edges of the article, the rearwardly diverging bend lines each forming an angle with the longitudinal centerline of from about 10° to about 80°;

wherein the main rear bend line folds so that the portions of the garment surface on opposite sides of the main rear bend line are brought closer together to provide a raised portion along the main rear bend line adapted to be in intimate contact with a user's body; and the main front bend line and the two rearwardly diverging bend lines fold so that the portions of the body surface on opposite sides of the main front bend line and the two rearwardly diverging bend lines are brought closer together to provide a recessed portion along the main front bend line adapted to be remote from a user's body, and wherein said topsheet, said backsheet, and said absorbent core provide said pre-folded configuration to said absorbent article.

32. The article of claim 31 wherein the side flaps comprise a user surface facing upwardly towards a user and a garment surface facing away from a user when the article is placed into a user's undergarment.

33. The article of claim 32 wherein garment surface of the flaps comprise attachment elements with which to secure the article to a user's undergarment.

34. The article of claim 31 wherein the bend lines are selected from the group consisting of pre-established fold lines, embossed channels or mixtures thereof.

35. The article of claim 34 wherein the bend lines form a "V" shape with the main front bend line and an inverted "V" shape with the main rear bend line.

36. The article of claim 34 wherein the thickness of the article is from about 1 mm to about 13 mm.

37. The article of claim 36 wherein the thickness of the article is uniform throughout its length.

38. The article of claim 34 wherein the main rear bend line begins at a point about one-fourth to about one-half of the distance away from the front edge and extends to about the rear edge of the article; the main front bend line begins at about the front edge and extends up to about the beginning point of the main rear bend line; and wherein the two rearwardly diverging bend lines start at about the beginning point of the main rear bend line, the rearwardly diverging bend lines each forming an angle with the longitudinal centerline of from about 15° to about 60°.

39. The article of claim 38 wherein the rearwardly diverging bend lines each form an angle with the longitudinal centerline of from about 20° to about 45°.

40. The article of claim 34 wherein the main rear bend line begins at a point about one-fourth to about one-half of the distance away from the front edge and extends to about the rear edge of the article; the main front bend line comprises two parallel bend lines beginning at about the front edge and extending to about the beginning of the main rear bend line, and wherein the two rearwardly diverging bend lines start at about the beginning point of the main rear bend line, the rearwardly diverging bend lines each forming an angle with the longitudinal centerline of from about 15° to about 60°.

41. The article of claim 38 wherein the rearwardly diverging bend lines each form an angle with the longitudinal centerline of from about 20° to about 45°.

42. The article of claim 36 wherein the main rear bend line begins at a point about one-third to about one-half of the distance away from the front edge and extends to about the rear edge of the article; the main front bend line begins at about the front edge and extends up to about the beginning point of the main rear bend line; and wherein the two rearwardly diverging bend lines start at about the beginning point of the main rear bend line, the rearwardly diverging bend lines each forming an angle with the longitudinal centerline of from about 15° to about 60°.

43. The article of claim 42 wherein the rearwardly diverging bend lines each form an angle with the longitudinal centerline of from about 20° to about 45°.

44. The article of claim 34 wherein the main rear bend line begins at a point about one-third to about one-half of the distance away from the front edge and extends to about the rear edge of the article; the main front bend line comprises two parallel bend lines beginning at about the front edge and extending to about the beginning of the main rear bend line, and wherein the two rearwardly diverging bend lines start at about the beginning point of the main rear bend line, the rearwardly diverging bend lines each forming an angle with the longitudinal centerline of from about 15° to about 60°.

45. The article of claim 44 wherein the rearwardly diverging bend lines each form an angle with the longitudinal centerline of from about 20° to about 45°.

46. The article of claim 34 wherein the bend lines form a "U" shape with the main front bend line and an inverted "U" shape with the main rear bend line.

47. The article of claim 34 wherein the bend lines form a "U" shape and a "V" shape with the main front and main rear bend lines.

* * * * *